United States Patent [19]
Kolff et al.

[11] Patent Number: 5,158,539
[45] Date of Patent: Oct. 27, 1992

[54] DEVICE AND METHOD FOR PREVENTING ASPIRATION OF AIR IN CARDIOPULMONARY BYPASS PATIENTS

[76] Inventors: Jacob Kolff, 1125 Brynlawn Rd., Villanova, Pa. 19085; David Wurzel, 2932 Woodview Dr., Hatfield, Pa. 19440

[21] Appl. No.: 474,482

[22] Filed: Feb. 2, 1990

[51] Int. Cl.⁵ ............................................. A61M 1/00
[52] U.S. Cl. ...................................... 604/31; 604/247; 128/DIG. 3; 137/855; 251/342
[58] Field of Search .................. 604/31, 30, 246, 247, 604/27, 28, 123, 4-6, 247; 128/DIG. 3; 137/855; 251/342; 210/645-647, 136; 422/44-48

[56] References Cited

U.S. PATENT DOCUMENTS

| | | | |
|---|---|---|---|
| 274,447 | 3/1883 | Kennish | 604/256 |
| 2,867,213 | 1/1959 | Thomas, Jr. | 604/247 |
| 3,536,451 | 10/1970 | Ludwin | 422/45 |
| 3,570,672 | 3/1971 | Bach | 210/136 |
| 4,160,383 | 7/1979 | Rauschenberger | 604/247 |
| 4,502,502 | 3/1985 | Krug | 604/247 |
| 4,540,406 | 9/1985 | Miles | 604/4 |
| 4,573,883 | 3/1986 | Noon et al. | 128/DIG. 3 |
| 4,650,457 | 3/1987 | Morioka et al. | 128/DIG. 3 |
| 4,671,786 | 6/1987 | Krug | 604/247 |
| 4,725,266 | 2/1988 | Siposs | 604/247 |
| 4,758,224 | 7/1988 | Siposs | 604/247 |
| 4,932,612 | 5/1990 | Trivett et al. | 210/646 |

FOREIGN PATENT DOCUMENTS

| | | | |
|---|---|---|---|
| 3512314 | 10/1986 | Fed. Rep. of Germany | 604/247 |
| 8704079 | 7/1987 | PCT Int'l Appl. | 604/247 |

Primary Examiner—Stephen C. Pellegrino
Assistant Examiner—Ralph A. Lewis
Attorney, Agent, or Firm—Thorpe, North & Western

[57] ABSTRACT

A method and device for protecting the circulatory system of a patient from incurring injury from inadvertent passage of air into the aorta when elevated with respect to and supported by a heart-lung machine and associated nonocclusive pump. This device and method provides positioning a valve means having unidirectional flow properties within the extracorporeal blood line connecting the heart-lung machine and patient. The valve is configured to offer nominal resistance against blood being returned to the patient, while blocking blood flow from the patient to the heart-lung machine.

2 Claims, 2 Drawing Sheets

DEVICE AND METHOD FOR PREVENTING ASPIRATION OF AIR IN CARDIOPULMONARY BYPASS PATIENTS

BACKGROUND OF THE INVENTION

1. Field of Invention

This invention relates to control of blood flow in an arterial bloodline utilized to return blood to the aorta or femoral artery of a patient being supported on a heart-lung machine as part of a cardiopulmonary bypass procedure. More specifically, the present invention relates to a device and method for preventing aspiration of air through sutures into the natural aorta or femoral artery by reason of a siphoning effect within the blood line when the associated pump returning the blood becomes defective or inoperable.

2. Prior Art

It is estimated that over 300,000 cardiopulmonary bypass operations are performed annually within the United States alone. This procedure is illustrated in FIG. 1 wherein the patient's circulatory system 10 is linked to a heart-lung machine 11 which includes an oxygenation unit 12 and pumping device 13. Blood is sucked from the superior and inferior vena cava 14 through venous cannulae 15 and 16. This blood is oxygenated in the artificial lung 12 and is pumped back to the circulatory system by pump 13 through an arterial blood line 17 feeding into the patient's aorta. Although the pump 13 is shown following the oxygenator 12, current trend is to position this pump in the circuit preceding the oxygenator, as illustrated in the configuration of FIG. 2.

For many years, the blood pump 13 utilized in the bypass procedure was a roller-pump design wherein the arterial blood line 17 was occluded by the pumping members. In approximately 1984-85, nonocclusive pumps were introduced and have since gained increasing favor as part of the bypass procedure. Currently, approximately 20% of the 300,000 cardiopulmonary bypass operations are serviced by non-occlusive pumps which incorporate structure similar to a rotary member such as used in the Biomedicus Pump (TM).

Although the rotary pump offers many advantages over prior occlusive pumps, the nonocclusive nature of the rotary pump poses a structural deficiency which may have serious repercussions on a patient upon malfunction or termination of pumping action of the rotor. This deficiency is illustrated in FIG. 2 wherein the respective venus cannulae 15 and 16 are graphically illustrated in the conventional attachment configuration for transferring blood to the pump 13. This pump 13 and attached oxygenator 12 are typically positioned under the patient 20 to facilitate gravity flow of blood from the patient to the pump and oxygenator system.

This configuration develops a column of blood of approximately 120 centimeters in height as illustrated by distance arrow 21. This is equivalent to fluid pressure of approximately 90 millimeters of mercury.

The pump 13 serves to overcome this pressure and return blood through the arterial blood line 17 to a femoral artery 18 for delivery to a femoral artery or to the aorta. If the pump 13 fails to supply enough pumping force to overcome the fluid pressure of the blood, the effect of gravity causes reverse flow of the blood in the arterial blood line 17 and develops a siphoning effect as blood flows back into the pump 13/oxygenator 12.

As a consequence, a subatmospheric pressure is created in the femoral artery or aorta such that air can be aspirated through suture lines or from other sources. This air then accumulates in the aorta and in the associated arterial blood line. In such an emergency situation, the attention of the perfusionist may be directed toward the failing pump and he may forget to clamp the arterial blood line tube 17. If the pump is then started, the perfusionist may transmit air from the tubing into the aorta. Even worse, concealed air within the aorta may pass into the patient's circulatory system causing an air embolism. Such occurrences have proved fatal for a number of patients.

The fact that the arterial blood line 17 is typically transparent does not always give adequate early visual warning to the perfusionist upon occurrence of such pump failure. Much of the upper transparent blood line 17 is concealed under patient covers, blocking view of entrained air. It will be noted that detection of air within the lower arterial blood line means that air has already been siphoned into the aorta (not visible to the perfusionist). Under current procedures, the perfusionist is responsible to monitor against such pump failure and siphoning of blood. Typically, the perfusionist must mechanically clamp the arterial blood line 17 upon detection of pump failure and then evaluate the extent of potential aspiration of air within the circulatory system. Detection of any air requires correction before reinstating blood flow, thereby creating a further life threatening situation.

OBJECTS AND SUMMARY OF THE INVENTION

It is an object of the present invention to provide a device and method for coupling within the arterial blood line for automatically blocking reverse flow of blood to thereby preclude the referenced siphoning effect and attendant aspiration of air.

It is a further object of the present invention to provide a device and method for occluding the arterial blood line along the reverse direction, but permitting free flow of blood in its return path to the patient's aorta.

Yet another object of the present invention is to provide a device and method which permits manual release of the check valve or occluding means such that blood within the arterial blood line can be passed to the oxygenator at the discretion of the perfusionist.

These and other objects are realized in a method and device for protecting the circulatory system of a patient from injury from inadvertent passage of air into the natural aorta when elevated with respect to and supported by a heart-lung machine and associated nonocclusive pump. This method comprises a step of positioning a valve means having unidirectional flow properties within the extracorporal arterial blood line such that the valve offers nominal resistance against blood being returned to the patient, but blocks blood flow from the patient to the heart-lung machine.

Other objects and features of the present invention will be apparent to those skilled in the art based upon the following detailed description, taken in combination with the accompanying drawings.

DETAILED DESCRIPTION OF THE INVENTION

Figure 1:
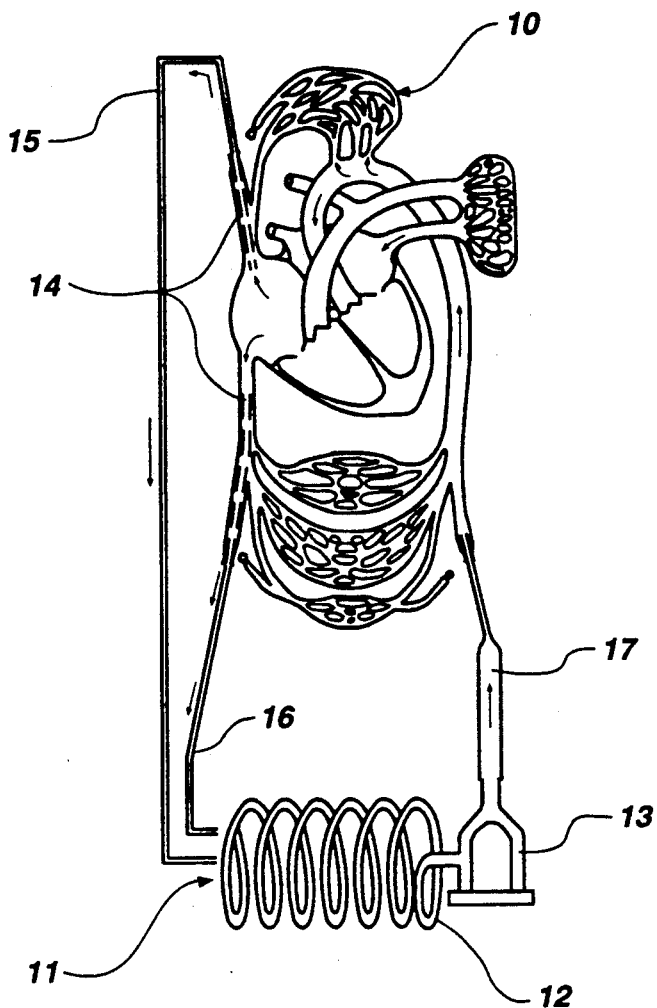
FIG. 1 shows a graphic illustration of a typical cardiopulmonary bypass procedure with associated heart-lung apparatus as currently known within the prior art.
Figure 2:
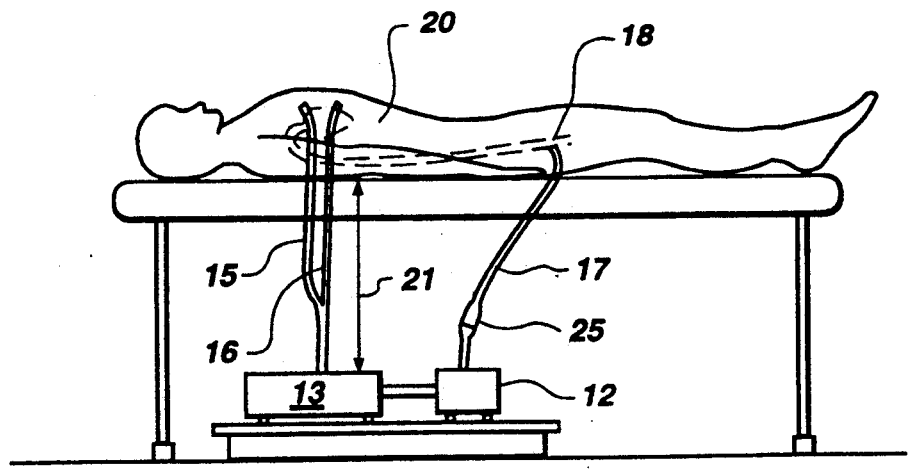
FIG. 2 graphically illustrates the present invention with a preferred relative placement configuration for the oxygenator, blood pump and associated flow lines with respect to an elevated patient.
Figure 3:
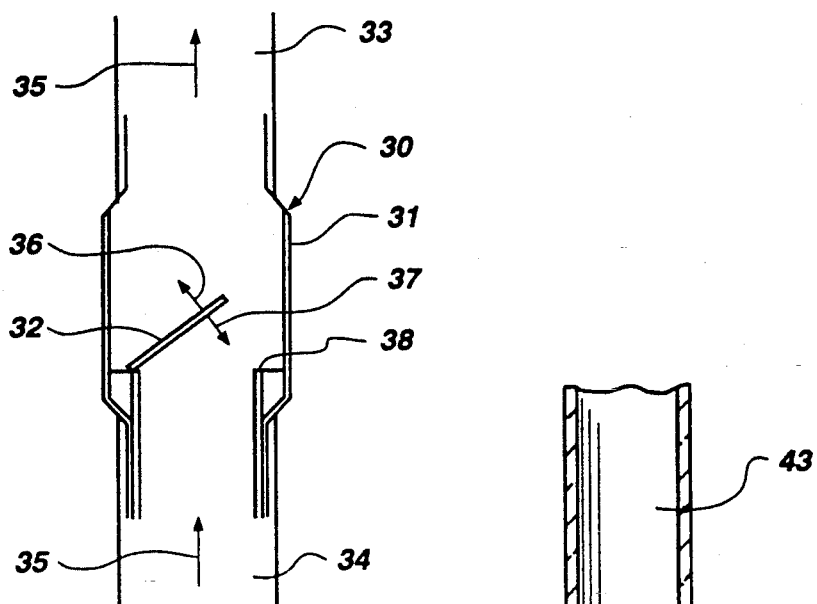
FIG. 3 is a schematic representation of a check valve as disclosed in the present invention.
Figure 4:
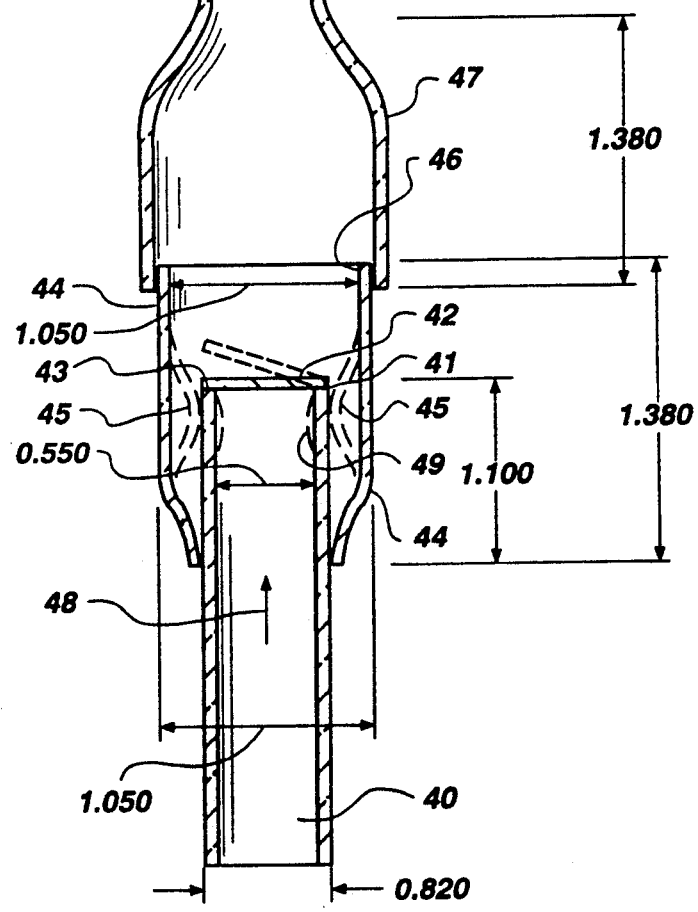
FIG. 4 graphically represents a check valve constructed in accordance with the present invention and shown in cross sectional detail.

The present invention incorporates a uni-directional check valve 25 within the arterial blood line 17 as shown in FIG. 2. This valve is illustrated in FIGS. 3 and 4 in greater detail. For example, FIG. 3 shows the valve generally 30, including a valve body 31 and occluding member 32. This valve is positioned in line between tube sections 33 and 34 which comprise the arterial blood line. The occluding member 32 is configured to be uni-directional in operation and is structurally constructed to provide low resistance against blood flow 35 which has been oxygenated and is being returned to the patient. In this mode, the occluding member 32 merely displaces out of the flow line as indicated by arrow 36. This is the position of the occluding member during operation of the heart-lung machine.

If for some reason the pump stops, the occluding member or check valve 32 is designed to prevent back flow of blood into the heart-lung machine, thereby preventing aspiration of air into the aorta. Upon such interruption, the reverse flow of blood physically displaces the occluding member 32 downward (as shown by arrow 37) until it seats at its periphery on valve seat 38. The check valve 32 is structured to be capable of withstanding the 90 millimeters Hg of pressure and thereby prevent back flow and consequential siphoning within the arterial blood line.

FIG. 4 illustrates one embodiment of the subject check valve, with dimensions as depicted in inches. The lower tubular member 40 extends to the oxygenator 12 as illustrated in FIG. 2. An upper end 41 of this tube includes the check valve or occluding member 42 which seats on a flat face or valve seat 43 formed at the end of the tube. This end of the tube and attached check valve 42 are coupled in line with the upper section of the arterial blood line 43 by means of the surrounding valve body 44. This valve body is also of transparent material similar to the tube 40 and 43. In addition, the valve body is provided with flexibility to enable its deflection as illustrated by phantom lines 45. The purpose of this construction will be discussed hereafter.

An upper end 46 of the valve body 44 is configured to telescopically insert within the inner diameter of a terminal section 47 of the upper arterial blood line 43. These two sections are sealed together to form a continuous flow line for delivery of returning blood 48 to the patient. During such flow, the check valve 42 displaces to an open configuration, allowing the blood to continue its circulation. Upon pump failure, or any other cause for reverse flow, the check valve 42 mechanically seats at the valve seat 43, blocking return of blood and precluding the referenced siphoning effect. It will be apparent that appropriate alarms can be triggered by this event, alerting the perfusionist to take remedial action. Once the problem is corrected, the pump can be restarted without concern that air has been aspirated into the aorta. This is in contrast with prior art systems which required the blood line to be purged of air before restarting the pump.

Furthermore, on completion of the bypass procedure, the valve body 44 can be squeezed as illustrated by phantom lines 45, thereby displacing tube structure 49 to break the seal of the check valve 42. The entrained column of blood within the arterial blood line is then allowed to flow back into the oxygenator.

In the illustrated embodiment of FIG. 4, the respective tube sections of the arterial flow line 40 and 43 are constructed of PVC or polyurethane. The occluding member 42 is fabricated of hard polyurethane, and has a thickness of approximately 0.040 inches. This check valve or occluding member is sealed with soft polyurethane (Pellethane 2363 AE) TM at one edge to the valve seat 43 to enable hinge displacement at the point of sealed contact.

It will be noted from the figures that the subject check valve is positioned in the lower half of the arterial blood line. This not only displaces the valve further from the patient's circulatory system, but also takes advantage of the greater fluid pressure applied by the column of blood supported within the arterial blood line above the check valve. Although specific compositions have been identified for the check valve and valve body, it is to be understood that any valve configuration can be applied to implement the concepts set forth herein. The selection of a flap valve as illustrated in FIGS. 3 and 4 requires identification of appropriate dimensions and characteristics to provide unidirectional flow properties within the blood line such that the valve opens in response to fluid pressure developed by the pump and closes in response to back flow of blood which may arise upon cessation of pumping action. The flap valve must have sufficient thickness to bear the pressure of the column of blood entrained within the flow line.

Similarly, the pinch-release illustrated in FIG. 4 can be developed by any releasing structure which permits an operator to open the valve occluding member despite the presence of fluid pressure or other sealing influences which activate the blocking action of the valve. The flexible material of valve body 44 provides an inexpensive mechanism for facilitating the partial collapse of the valve seat 43, thereby breaking the seal between that sea and the occluding member 42.

It is to be understood that the foregoing examples and description are provided for exemplary purposes and are not to be construed as limiting, except as set forth in the following claims.

We claim:

1. A method for preventing aspiration of ambient air through sutures or other openings formed in the circulatory system of a patient during perfusion of blood through a heart-lung bypass device, comprising the steps of:

positioning the patient in an elevated location with respect to the heart-lung device;

coupling a nonocclusive blood pumping means in fluid line with the heart-lung device;

coupling an extracorporeal arterial blood line in fluid communication between the pumping means and the patient's circulatory system such that the extracorporeal arterial blood line provides containment for a column of blood which is subject to gravity forces generating a positive pressure head with respect to blood flowing therein;

positioning a unidirectional valve means within the extracorporeal arterial blood line such that the valve means offers nominal resistance against blood being returned against gravity to the patient, but blocks reverse blood flow from the patient to the heart-lung device when the positive pressure of the column of blood overcomes pumping forces of the pumping means, thereby preventing a siphoning effect within the patient's circulatory system wherein the reverse blood flow would result in sub-atmospheric pressure within the circulatory system, leading to aspiration of ambient air through the sutures and other openings therein;

further comprising the step of providing the valve means with releasing structure which permits an operator to open the valve means despite the presence of sealing influences which activate the blocking action of the valve means, thereby allowing the operator to discharge blood entrained within the blood line into the heart-lung machine following detachment of an upper end of the blood line from the circulatory system of the patient.

2. A method as defined in claim 1 wherein the step of providing releasing structure includes the more specific step of structuring the valve means and surrounding supporting structure of the blood line with sufficient flexibility to permit partial collapse thereof, breaking the seal of the valve means to allow blood flow therethrough.

* * * * *